(12) United States Patent
Lee

(10) Patent No.: US 8,876,531 B2
(45) Date of Patent: Nov. 4, 2014

(54) NON-REMOVABLE BRIDGE DENTAL PROSTHESIS

(76) Inventor: Il-Hong Lee, Busan (KR)

(*) Notice: Subject to any disclaimer, the term of this patent is extended or adjusted under 35 U.S.C. 154(b) by 0 days.

(21) Appl. No.: 14/128,689

(22) PCT Filed: Jun. 18, 2012

(86) PCT No.: PCT/KR2012/004787
§ 371 (c)(1),
(2), (4) Date: Dec. 23, 2013

(87) PCT Pub. No.: WO2012/177025
PCT Pub. Date: Dec. 27, 2012

(65) Prior Publication Data
US 2014/0127642 A1 May 8, 2014

(30) Foreign Application Priority Data
Jun. 24, 2011 (KR) .................... 10-2011-0061513

(51) Int. Cl.
*A61C 13/10* (2006.01)
*A61C 13/225* (2006.01)
*A61C 13/271* (2006.01)
*A61C 13/267* (2006.01)

(52) U.S. Cl.
CPC ........... *A61C 13/2255* (2013.01); *A61C 13/267* (2013.01); *A61C 13/26* (2013.01)
USPC ........................................ 433/194

(58) Field of Classification Search
USPC ..................... 433/181–183, 191, 205, 219
See application file for complete search history.

(56) References Cited

U.S. PATENT DOCUMENTS

| 4,715,817 | A | * | 12/1987 | Zuest et al. | .................... 433/181 |
| 5,092,772 | A | * | 3/1992 | Seaton | .......................... 433/182 |
| 8,221,120 | B2 | * | 7/2012 | Jang | .............................. 433/194 |
| 2004/0086831 | A1 | | 5/2004 | Lai | |

FOREIGN PATENT DOCUMENTS

| KR | 10-2005-0014391 A | 2/2005 |
| KR | 10-2008-0026679 A | 3/2008 |
| KR | 10-0983311 B1 | 9/2010 |
| KR | 10-1009443 B1 | 1/2011 |

* cited by examiner

*Primary Examiner* — Sunil K Singh
(74) *Attorney, Agent, or Firm* — AKC Patents LLC; Aliki K. Collins

(57) ABSTRACT

A non-removable bridge dental prosthesis includes an artificial tooth to be inserted into a region from which a tooth has been lost, a bridge tightly fixed to the rear surfaces of the teeth on either side of the region from which the tooth was lost, and a coupling member for coupling the artificial tooth to the bridge. The coupling member is integrally installed on the rear surface of the artificial tooth, and has a catching piece and a coupling projection. A coupling hole is formed in the bridge in a shape corresponding to the coupling projection and is located at a position where the coupling projection of the coupling member is formed. The coupling projection is inserted in the coupling hole of the bridge and simultaneously, the catching piece is caught on the top end of the bridge.

4 Claims, 3 Drawing Sheets

NON-REMOVABLE BRIDGE DENTAL PROSTHESIS

CROSS-REFERENCE TO RELATED APPLICATION

This application claims the benefit of Korean Patent Application No. 10-2011-0061513, filed on Jun. 24, 2011 in the Korean Intellectual Property Office, the disclosure of which is incorporated herein by reference.

TECHNICAL FIELD

The present invention relates to a non-removable bridge dental prosthesis that can conveniently and safely perform a surgical operation of an artificial tooth that replaces a damaged tooth without an artificial tooth root or without removal of an adjacent tooth.

BACKGROUND ART

[Document 1] Korean Patent No. 10-0983311 (Sep. 14, 2010).

DETAILED DESCRIPTION OF INVENTION

Technical Problem

A crown bridge surgical operation method, which is one of dental prosthesis treatment methods generally used for restoring a damaged tooth is a surgical operation method of fixing an artificial tooth between healthy teeth by covering a cap formed at both sides of the artificial tooth at a healthy tooth positioned at both sides of the damaged tooth and has a problem that healthy teeth should be removed by a thickness of a cap so as to cover the cap at the healthy teeth positioned at both sides of the artificial tooth.

In order to solve the problem, the present inventor invented an invention of Document 1 formed with an artificial tooth inserted into a tooth extraction portion so as to easily perform a bridge surgical operation without damage of healthy teeth, a bridge that close contacts with and is fixed to a rear surface of teeth of both sides of the tooth extraction portion and that inserts and fixes the artificial tooth to the front side, and a coupling member that couples the artificial tooth and the bridge.

However, the invention of Document 1 has a defect having blade portions at both sides of an artificial tooth in order to prevent the artificial tooth from being pushed to the rear side, thereby injuring an aesthetic external appearance of teeth after a surgical operation.

Further, in a state in which an artificial tooth and a bridge are coupled, as a coupling member has a screw fastening structure, the invention of document 1 has a defect that it is inconvenient to perform a surgical operation in a narrow mouth.

The present invention has been made in view of the above problems, and provides a non-removable bridge dental prosthesis that can be securely fixed without removal of any tooth of a tooth extraction portion and that can easily perform a surgical operation through a structure in which both sides of an artificial tooth and both sides of the front side of a coupling member are formed to have an area larger than space formed by teeth of both sides of the tooth extraction portion and in which the coupling member integrally formed with the artificial tooth is inserted and fixed from the front side to the rear side of a bridge.

Technical Solution

In accordance with an aspect of the present invention, there is a non-removable bridge dental prosthesis formed with an artificial tooth inserted into a tooth extraction portion; a bridge that close contacts with and is fixed to a rear surface of teeth of both sides of the tooth extraction portion and in which the artificial tooth is inserted and fixed to the front side; and a coupling member that couples the artificial tooth and the bridge, wherein at a rear surface of the artificial tooth, the coupling member is integrally installed, in an upper portion and an intermediate portion of the coupling member, a coupling protrusion and a latch piece inclined by a predetermined angle downward are protruded, in the bridge, at a position corresponding to a position in which the coupling protrusion of the coupling member is formed, a coupling hole is formed in a shape corresponding to the coupling protrusion, and by inserting the coupling member integrally installed in the artificial tooth into a tooth extraction portion in a diagonal direction, while the coupling protrusion is inserted into the coupling hole of the bridge fixed to the teeth of both sides of the tooth extraction portion, the latch piece is latched to an upper end portion of the bridge and thus the artificial tooth is securely fixed to the tooth extraction portion.

Advantageous Effects

According to the present invention, as a non-removable bridge dental prosthesis is securely fixed to a tooth extraction portion when masticating food without removal of a tooth adjacent to the tooth extraction portion, a removal ratio of dental prosthesis is minimized, there is no exposed portion other than an artificial tooth and thus an aesthetic external appearance is provided, a coupling member is integrally installed with the artificial tooth, and thus a surgical operation can be conveniently performed without causing discomfort to a surgical operator and a patient.

BEST MODES FOR CARRYING OUT THE INVENTION

Figure 1:
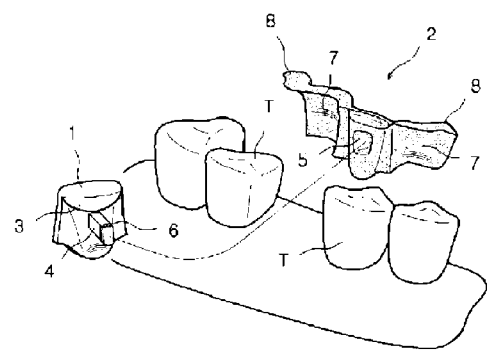
FIG. 1 is an exploded perspective view illustrating a non-removable bridge dental prosthesis according to a first exemplary embodiment of the present invention.

Hereinafter, an exemplary embodiment of the present invention will be described in detail with reference to the accompanying drawings.

A non-removable bridge dental prosthesis 100 according to an exemplary embodiment of the present invention is formed with an artificial tooth 1 inserted into a tooth extraction portion; a bridge 2 that close contacts with and fixed to a rear surface of teeth T of both sides of the tooth extraction portion and in which the artificial tooth 1 is inserted and fixed to the front side; and a coupling member that couples the artificial tooth 1 and the bridge 2.

At a rear surface of the artificial tooth 1, a coupling member is integrally installed, in an upper portion and an intermediate portion of the coupling member, a latch piece 3 and a coupling protrusion 4 inclined by a predetermined angle downward are protruded, and the bridge 2 has a coupling hole 5 formed in a shape corresponding to the coupling protrusion 4 at a position corresponding to a position in which the coupling protrusion 4 of the coupling member is formed.

In an end portion of the coupling protrusion 4, an adhesion groove 6 of a predetermined depth is formed, at the inside of the coupling hole 5, in a state in which the coupling protrusion 4 is inserted into the coupling hole 5, at a position corresponding to the adhesion groove 6, a coupling groove 5a is formed, and a distance between the rear side of the coupling hole 5 and the coupling groove 5a is larger than an inner diameter of the front side of the coupling hole 5 and is formed smaller than an inner diameter of the coupling groove 5a.

Both sides of the artificial tooth 1 and both sides of the front side of the coupling member are formed larger than space in which the teeth T of both sides of the tooth extraction portion are formed.

At both sides of the bridge 2, in a portion contacting with a rear surface of the teeth T of both sides of the tooth extraction portion, the same curved surface 7 as the rear surface of the teeth T is formed, and a support cover 8 that can cover a marginal ridge and a non-functional cusp of the teeth T is formed.

Here, a marginal ridge indicates teeth corner portion of a portion in which a tooth and a tooth contact in an adjacent teeth set.

A non-removable bridge dental prosthesis according to the present invention formed in this way is operated to enable a patient not to feel discomfort due to a damaged tooth in daily life by fixing the artificial tooth 1 to a tooth extraction portion of the damaged tooth.

Particularly, a non-removable bridge dental prosthesis according to the present invention is characterized in that when a mouth is opened, only the artificial tooth 1 is exposed to the outside and thus an aesthetic external appearance is provided, and as a coupling member installed in the artificial tooth 1 is inserted into the bridge 2 and is coupled to the bridge 2, a surgical operation is conveniently performed, and even if a force is applied to the front side and the rear side of the artificial tooth 1, a fixed state of the artificial tooth 1 is securely maintained.

Figure 2:
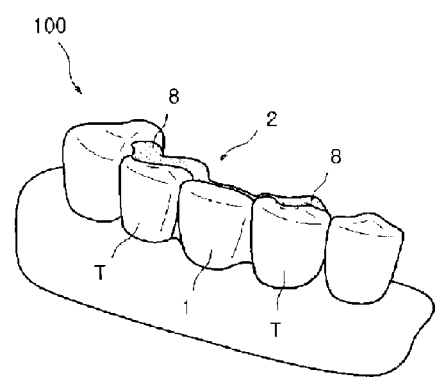
FIG. 2 is a perspective view illustrating a coupling state of FIG. 1.

As shown in FIGS. 1 and 2, while the artificial tooth 1 having a front surface larger than a width of space formed by the teeth T of both sides of the tooth extraction portion are formed is obliquely inserted into the coupling hole 5 of the bridge 2 by the coupling protrusion 4 of the coupling member installed at a rear surface of the artificial tooth 1, the latch piece 3 is latched and fixed to an upper end portion of the bridge 2, and the binder B is injected into the rear side of the coupling hole 5 and thus the coupling protrusion 4 is adhered and fixed.

Figure 3:
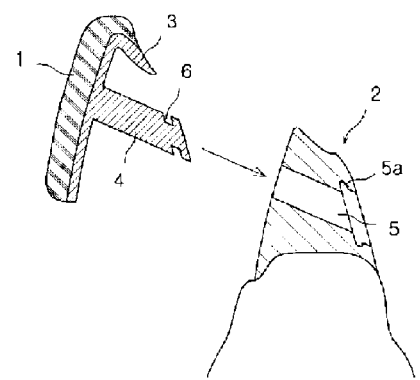
FIG. 3 is an exploded cross-sectional view illustrating a first exemplary embodiment of the present invention.
Figure 4:
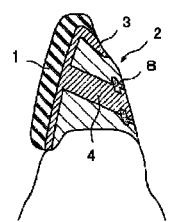
FIG. 4 is a cross-sectional view illustrating a coupling state of FIG. 3.

That is, as shown in FIGS. 3 and 4, when inserting and fixing a coupling member installed at a rear surface of the artificial tooth 1 to the bridge 2, a portion of the bridge 2 positioned between an upper end portion of the bridge 2 and the coupling hole 5 is inserted into space formed between the latch piece 3 of the coupling member and the coupling protrusion 4 to perform a function of a support.

Therefore, as the coupling member is obliquely coupled to the bridge 2 from an upper portion to a lower portion, a surgical operation is simpler than that of a conventional case through a structure in which the coupling member is inserted and fixed the coupling member and that can easily bear a force and a rotation occurring in the artificial tooth 1 when tearing food further than a structure in which the coupling member is horizontally coupled to the bridge 2 from the front side to the rear side.

Figure 5:
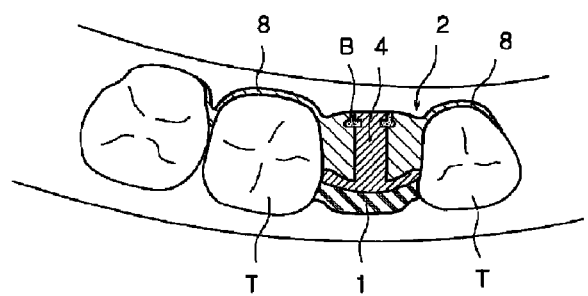
FIG. 5 is a horizontal cross-sectional view illustrating a coupling state of FIG. 3.
Figure 6:
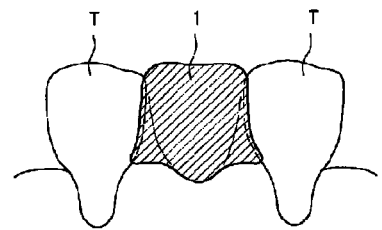
FIG. 6 is a front view of FIG. 2.
Figure 7:
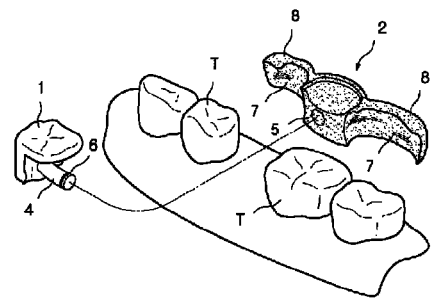
FIG. 7 is an exploded perspective view illustrating a non-removable bridge dental prosthesis according to a second exemplary embodiment of the present invention.
Figure 8:
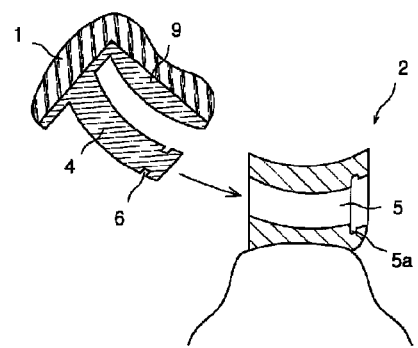
FIG. 8 is an exploded cross-sectional view illustrating a second exemplary embodiment of the present invention.
Figure 9:
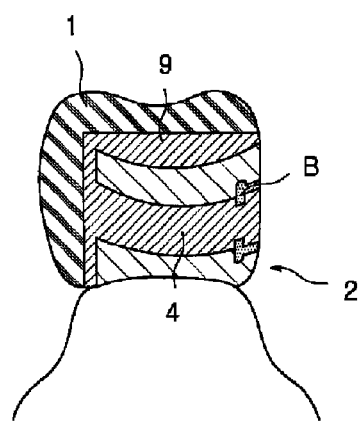
FIG. 9 is a cross-sectional view illustrating a coupling state of FIG. 8.
Figure 10:
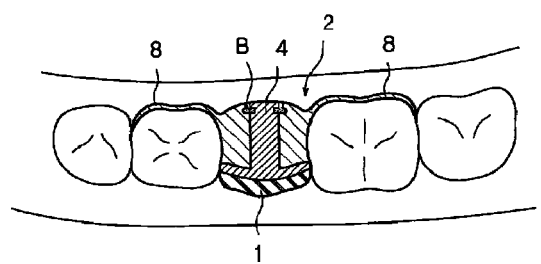
FIG. 10 is a horizontal cross-sectional view illustrating a coupling state of a second exemplary embodiment of the present invention.

Further, as shown in FIGS. 5 and 6, both sides of the artificial tooth 1 and both sides of the front side of the coupling member are formed larger than space formed by the teeth T positioned at both sides of the tooth extraction portion, and this is to prevent the artificial tooth 1 from being pushed to the rear side using the teeth T positioned at both sides of the tooth extraction portion as a support when chewing food or when an impact is applied from the outside.

Accordingly, even if the artificial tooth 1 is exposed, in order to prevent that the artificial tooth 1 is pushed to the rear side like a conventional case, because a blade portion installed at both sides of the artificial tooth 1 does not exist, other portions of the non-removable bridge dental prosthesis 100 other than the artificial tooth 1 are not exposed and thus an aesthetic external appearance is provided, and the non-removable bridge dental prosthesis is securely fixed by teeth of both sides of the tooth extraction portion T.

As shown in FIGS. 3 and 4, in an end portion of the coupling protrusion 4, the adhesion groove 6 of a predetermined depth is formed, and at the inside of the coupling hole 5, in a state in which the coupling protrusion is inserted into the coupling hole 5, at a position corresponding to the adhesion groove 6, the coupling groove 5a is formed, and a distance between the rear side of the coupling hole 5 and the coupling groove 5a is larger than an inner diameter of the front side of the coupling hole 5 and is formed smaller than an inner diameter of the coupling groove 5a, and thus the artificial tooth 1 is securely fixed to the bridge 2 through the binder B.

That is, when a binder B is injected into the rear side of the coupling hole 5 and fills the adhesion groove 6 and the coupling hole 5 to be solidified, even if a force of a front direction is applied to the artificial tooth 1, the binder B is latched to the adhesion groove 6 and the coupling groove 5a to support the artificial tooth 1.

Further, as the front side of the solidified binder B is formed larger than space between the rear aide of the coupling protrusion 4 and the rear aide of the coupling hole 5, the binder B is prevented from being withdrawn to the rear side due to an impact and thus the artificial tooth 1 can be securely fixed to the bridge 2.

As shown in FIG. 1, in the bridge 2, the curved surface 7 and a support cover 8 are formed to be securely fixed to the teeth T positioned at both sides of the tooth extraction portion as well as the coupling hole 5 formed in the tooth extraction portion.

This is to secure a fixing area for fixing the bridge 2 to the maximum through the curved surface 7 and the support cover 8 so as to securely fix the bridge 2 to the teeth T in consideration of an engagement relationship of an upper jaw and a lower jaw and a structure of teeth.

Further, by applying a binder at the curved surface 7 of the bridge 2 and an inner side surface of the support cover 8, by securely adhering and fixing to the teeth T positioned at both sides of the tooth extraction portion, the artificial tooth 1 is securely fixed against a force or a rotation occurring when masticating food.

A first exemplary embodiment of the present invention formed in this way has a structure to be applied to teeth used for tearing food, such as a front tooth and a canine tooth, and by changing the first exemplary embodiment, a second exemplary embodiment of the present invention to be applied to a premolar and a molar may be formed.

In this case, in a second exemplary embodiment shown in FIGS. 7 to 10, in a configuration of a first exemplary embodiment, a support piece 9 horizontally protruded in an upper portion of the coupling member and having a lower surface formed in a curved shape is formed instead of a latch piece 3, and a coupling protrusion 4 is protruded in the same shape as a curved surface of a lower surface of the support piece 9.

Therefore, the artificial tooth 1 of a premolar or molar form coupled to a bridge 2 through a coupling member of the second exemplary embodiment can easily support a force operating to the front side and a compression force occurring in a vertical direction.

That is, similar to the first exemplary embodiment, the coupling member of the artificial tooth 1 is latched to the bridge 2 inserted between the support piece 9 and the coupling protrusion 4 to support a force operating to the front side, and the support piece 9 is horizontally formed similar to a structure in which an upper surface of a premolar and a molar are widely formed to easily bear a force of a vertical direction operating to an upper surface of the artificial tooth 1.

In a surgical operation of a second exemplary embodiment, similar to the first exemplary embodiment, the bridge 2 is adhered and fixed by a binder to a rear surface of the teeth T positioned at both sides of the tooth extraction portion, and by inserting the coupling protrusion 4 of a coupling member integrally installed in the artificial tooth 1 in a diagonal direction into a coupling hole 5 of the bridge 2 positioned at the tooth extraction portion, an end portion of the coupling protrusion 4 protruded to a rear surface of the bridge 2 is adhered and fixed by a binder B.

In this way, a non-removable bridge dental prosthesis 100 according to an exemplary embodiment of the present invention is securely fixed to a tooth extraction portion when masticating food without removing a tooth T adjacent to a tooth extraction portion and thus a separation ratio of the non-removable bridge dental prosthesis 100 is minimized and there is no exposed portion other than the artificial tooth 1 and thus an aesthetic external appearance is provided, and as the coupling member is integrally installed in the artificial tooth 1, a surgical operator and a patient can conveniently have a surgical operation without discomfort.

The invention claimed is:

1. A non-removal bridge dental prosthesis comprising:
an artificial tooth (1) configured to be inserted into a tooth extraction portion;
a bridge (2) that close contacts with and is fixed to a rear surface of teeth (T) of both sides of the tooth extraction portion and in which the artificial tooth (1) is inserted and fixed to the front side;
a coupling member that couples the artificial tooth (1) and the bridge (2);
wherein at a rear surface of the artificial tooth (1), the coupling member is integrally installed, and wherein in an upper portion and an intermediate portion of the coupling member, a support piece (9) and coupling protrusion (4) are protruded, respectively;
wherein in the bridge (2), at a position corresponding to a position in which the coupling protrusion (4) of the coupling member is formed, a coupling hole (5) is formed in a shape corresponding to the coupling protrusion (4);
wherein the support piece (9) is formed horizontally in the upper portion of the coupling member and comprises a curved lower surface; and
wherein the coupling protrusion (4) is formed in the same shape as that of the curved tower surface of the support piece (9).

2. The non-removable bridge dental prosthesis of claim 1, wherein in an end portion of the coupling protrusion (4), an adhesion groove (6) of a predetermined depth is formed, and at an inner surface of the coupling hole (5), in a state in which the coupling protrusion (4) is inserted into the coupling hole (5), at a position corresponding to a adhesion groove (6), a coupling groove (5a) is formed, and a distance between the rear side of the coupling hole (5) and the coupling groove (5a) is larger than an inner diameter of the front side of the coupling hole (5) and is formed smaller than an inner diameter of the coupling groove (5a), and a binder (B) is injected into the rear side of the coupling hole (5) and thus the artificial tooth (1) is securely adhered and fixed to the bridge (2).

3. The non-removable bridge dental prosthesis of claim 1, wherein both sides of the artificial tooth (1) and both sides of the front side of the coupling member are formed larger than space in which the teeth (T) of both sides of the tooth extraction portion are formed, and even if a force is applied from the front side to the rear side of the artificial tooth (1), both sides of the artificial tooth (1) and both sides of the front side of the coupling member are securely latched and fixed to the tooth (T) of the both sides of the tooth extraction portion and thus the artificial tooth (1) is prevented from being pushed to the rear side.

4. A non-removal bridge dental prosthesis comprising:
an artificial tooth (1) configured to be inserted into a tooth extraction portion;
a bridge (2) that close contacts with and is fixed to a rear surface of teeth (T) of both sides of the tooth extraction portion and in which artificial tooth (1) is inserted and fixed to the front side;
a coupling member that couples the artificial tooth (1) and the bridge (2);
wherein at a rear surface of the artificial tooth (1), the coupling member is integrally installed, in an upper portion and an intermediate portion of the coupling member, coupling protrusion (4) and a latch piece (3) inclined by a predetermined angle downward are protruded;
wherein in the bridge (2), at a position corresponding to a position in which the coupling protrusion (4) of the coupling member is formed, a coupling hole (5) is formed in a shape corresponding to the coupling protrusion (4), and by inserting the coupling member integrally installed in the artificial tooth (1) into the tooth extraction portion in a diagonal direction, while the coupling protrusion (4) is inserted into the coupling hole (5) of the bridge (2) fixed to the teeth (T) of both sides of the tooth extraction portion, the latch piece (3) is latched to an upper end portion of the bridge (2) and thus the artificial tooth (1) is securely fixed to the tooth extraction portion; and
wherein in an end portion of the coupling protrusion (4), an adhesion groove (6) of a predetermined depth is formed, and at an inner surface of the coupling hole (5), in a state in which the coupling protrusion (4) is inserted into the coupling hole (5), at a position corresponding to a adhesion groove (6), a coupling groove (5a) is formed, and a distance between the rear side of the coupling hole (5) and the coupling groove (5*a*) is larger than an inner diameter of the front side of the coupling hole (5) and is formed smaller than an inner diameter of the coupling groove (5*a*), and a binder (B) is injected into the rear side of the coupling hole (5) and thus the artificial tooth (1) is securely adhered and fixed to the bridge (2).

\* \* \* \* \*